(12) United States Patent  
Anthony et al.

(10) Patent No.: US 8,328,725 B2
(45) Date of Patent: Dec. 11, 2012

(54) HANDHELD FORCE-CONTROLLED ULTRASOUND PROBE

(75) Inventors: Brian W. Anthony, Cambridge, MA (US); Matthew W. Gilbertson, Berea, KY (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/005,066

(22) Filed: Jan. 12, 2011

(65) Prior Publication Data

US 2011/0166453 A1 Jul. 7, 2011

Related U.S. Application Data

(63) Continuation of application No. 12/972,461, filed on Dec. 18, 2010.

(60) Provisional application No. 61/287,886, filed on Dec. 18, 2009.

(51) Int. Cl.
*A61B 8/14* (2006.01)
(52) U.S. Cl. ........................................... 600/459
(58) Field of Classification Search ................ 600/459
See application file for complete search history.

(56) References Cited

U.S. PATENT DOCUMENTS

| 7,597,664 B2 | 10/2009 | Jones et al. | |
| 2002/0035326 A1* | 3/2002 | Kamiyama | 600/437 |
| 2002/0068870 A1 | 6/2002 | Alam et al. | |
| 2004/0230214 A1* | 11/2004 | Donofrio et al. | 606/169 |
| 2004/0254460 A1 | 12/2004 | Burcher et al. | |
| 2007/0276292 A1 | 11/2007 | Hansma et al. | |
| 2009/0149752 A1 | 6/2009 | Osaka et al. | |
| 2009/0306509 A1 | 12/2009 | Pedersen et al. | |
| 2009/0306515 A1 | 12/2009 | Matsumura et al. | |
| 2010/0204694 A1 | 8/2010 | Mehta et al. | |
| 2011/0152690 A1 | 6/2011 | Anthony et al. | |
| 2011/0172541 A1 | 7/2011 | Anthony et al. | |

FOREIGN PATENT DOCUMENTS

WO WO-2011/075713 A1 6/2011

OTHER PUBLICATIONS

"International Application Serial No. PCT/US10/61179, Search Report and Written Opinion mailed Mar. 22, 2011", , 17.
Marchal, Maud "A one-DOF freehand haptic device for robotic tele-echography", *Studies in Health Technology and Informatics 98* 2004, 231-233.
Stolka, Philipp J. et al., "Multi-DoF Probe Trajectory Reconstruction with Local Sensors for 2D-to-3D Ultrasound", Biomedical Imaging: From Nano to Macro 2010 IEEE International Symposium Apr. 14-17, 2010 Apr. 14, 2010 , pp. 316-319.
Stolka, Philipp J. et al., "5-DoF Trajectory Reconstruction for Handheld Ultrasound with Local Sensors", 2009 IEEE International Ultrasonics Symposium Proceedings 2009 , pp. 1864-1867.

(Continued)

*Primary Examiner* — Brian Casler
*Assistant Examiner* — Saurel J Selkin
(74) *Attorney, Agent, or Firm* — Strategic Patents, P.C.

(57) ABSTRACT

A handheld ultrasound probe includes force detection and feedback to permit control and/or characterization of applied forces. The probe may, for example, be operated to maintain a substantially constant applied force over a period of use independent of a user's hand position, or to measure applied forces that might contribute to deformation of an imaging subject.

18 Claims, 5 Drawing Sheets

OTHER PUBLICATIONS

Goldsmith, A M. et al., "An Inertial-Optical Tracking System for Portable, Quantitative, 3D Ultrasound", 2008 IEEE International Ultrasonics Symposium Proceedings 2008 , pp. 45-49.

Poulsen, Carsten et al., "An Optical Registration Method for 3D Ultrasound Freehand Scanning", 2005 IEEE Ultrasonics Symposium 2005 , pp. 1236-1240.

"U.S. Appl. No. 12/972,461, Non-Final Office Action mailed Mar. 14, 2012", , 11.

"U.S. Appl. No. 13/005,143, Non-Final Office Action mailed Mar. 15, 2012".

"U.S. Appl. No. 12/972,461, Notice of Allowance mailed Oct. 3, 2012", SN12972461 NPL-14 Oct. 3, 2012 , 13 pgs.

* cited by examiner

HANDHELD FORCE-CONTROLLED ULTRASOUND PROBE

CROSS-REFERENCE TO RELATED APPLICATIONS

This application is a continuation of U.S. patent application Ser. No. 12/972,461 filed Dec. 18, 2010, which claims the benefit of provisional application 61/287,886 filed Dec. 18, 2009 and entitled "HANDHELD FORCE-CONTROLLED ULTRASOUND PROBE," each of which is hereby incorporated by reference in its entirety.

BACKGROUND

Medical imaging technologies permit viewing of internal body structures and anatomy without invasive surgical procedures. Ultrasound imaging, in particular, allows a physician to visualize internal details of soft tissue, organs, and the like by propagating sonic waves through a body and detecting sonic waves as they reflect off various internal structures. While current ultrasound techniques can provide useful diagnostic and treatment information, data for ultrasound imaging is generally captured with a handheld probe that is pressed against a body surface until suitable contact forces are achieved for imaging.

For example, in a medical imaging context, an ultrasound technician grasps an ultrasound probe and places the probe in contact with a patient's skin. A transducer on the probe emits ultrasonic acoustic waves into the patient and measures reflections of the waves. These measurements may be converted into images for visualization of internal anatomical structures. In general, the harder an ultrasound probe is pressed into the skin, the better the waves penetrate the skin's surface and the higher the signal-to-noise ratio (SNR) of resultant images. However, for soft areas of the body, varying the contact force of the ultrasound probe also tends to deform the internal structure of the patient's tissue. As a result, images of the same patent's tissue may show different deformations of the internal structures due to varying contact forces used when acquiring the images. This may lead to difficulties in medical diagnosis, such as where a tumor in one ultrasound image appears to be larger than the same tumor shown in an earlier-acquired image. It may be difficult or impossible to determine whether the tumor has grown, or if the tumor was merely deformed differently by ultrasound probe when the images were acquired.

Thus, as a significant disadvantage, the use of handheld probes may require a substantial exercise of skill and dexterity from a user to achieve consistent results, and typically involves an application of force that deforms imaged structures in a quantitatively uncharacterized manner. There remains a need for ultrasound imaging techniques that permit characterization and/or control of deformation forces acting upon an imaging subject.

SUMMARY

A handheld ultrasound probe includes force detection and feedback to permit control and/or characterization of applied forces. The probe may, for example, be operated to maintain a substantially constant applied force over a period of use independent of a user's hand position, or to measure applied forces that might contribute to deformation of an imaging subject.

A device disclosed herein includes an ultrasound transducer; a force sensor mechanically coupled to the ultrasound transducer and configured to sense an instantaneous contact force between the ultrasound transducer and a subject; a linear drive system mechanically coupled to the ultrasound transducer and including a control input, the linear drive system responsive to a control signal received at the control input to translate the ultrasound transducer along an actuation axis; and a controller electronically coupled to the force sensor and the control input of the linear drive system, the controller including processing circuitry configured to generate the control signal to the control input in a manner that maintains a substantially constant predetermined contact force between the ultrasound transducer and the subject.

The linear drive system and the controller may be configured to compensate for an oscillating hand movement of a user at a frequency between four Hertz and thirty Hertz. The force sensor may have a resolution of at least 0.05 Newtons. The linear drive system may provide an actuation range for the ultrasound transducer of at least six centimeters. The device may include a torque sensor mechanically coupled to the ultrasound transducer and electronically coupled to the controller, the torque sensor detecting a torque between the ultrasound transducer and the linear drive system. The device may include a proximity sensor operable to detect a proximity of the ultrasound transducer to the subject. The device may include an orientation sensor operable to independently detect at least one of a position and an orientation of the device. The controller may be programmed to vary the contact force according to a generalized tent map function. The device may include a memory to store data from the ultrasound transducer and the sensor. The device may include a wireless interface for communication with a remote storage device. The device may include a display to display at least one ultrasound image obtained from the ultrasound transducer. The display may display the instantaneous contact force. The device may include at least one limit switch to detect an end of travel of the linear drive system along the actuation axis. The device may include a user input to receive an input from the user during an ultrasound scan. The user input may include a button for user activation of a function including at least one of initiation of a scan, termination of a scan, selection of the instantaneous contact force as the substantially constant predetermined contact force, storage of the instantaneous contact force in a memory for subsequent recall, and recall of the substantially constant predetermined contact force from the memory. The user input may include at least one of a button, a switch, and a dial.

The controller may provide at least three modes of operation including an initiation mode, a controlled-force mode, and a scan termination mode. The controller may provide an initiation mode in which the linear drive system is placed in a neutral position and the force sensor is measured to monitor the instantaneous contact force, the controller transitioning to controlled-force operation when the instantaneous contact force meets a predetermined threshold. The controller may provide a scan termination mode in which control of the linear drive system transitions from a controlled-force operation to a controlled-velocity operation. The controlled-velocity operation may return the linear drive system to a neutral position.

A method disclosed herein includes identifying a predetermined, desired contact force between the handheld ultrasound probe and a target; measuring a current contact force between the handheld ultrasound probe and the target; comparing the current contact force to the desired contact force, thereby identifying a force differential; and actuating a linear drive system to move the handheld ultrasound probe along an actuation axis so as to reduce the force differential.

The method may include calibrating at least one of a force sensor and a torque sensor mechanically coupled to the handheld ultrasound probe to account for a weight of the handheld ultrasound probe. The method may include calibrating at least one of a force sensor and a torque sensor mechanically coupled to the handheld ultrasound probe to account for a mounting angle of the ultrasound probe. The predetermined desired contact force may be constant. The predetermined desired contact force may be less than or equal to twenty Newtons. The predetermined desired contact force may vary with time. The predetermined desired contact force may vary according to a generalized tent map function.

The method may include wirelessly transmitting ultrasound data to a remote storage facility. The method may include detecting a proximity of the handheld ultrasound probe to the target. The method may include detecting at least one of a position and an orientation of the handheld ultrasound probe using an orientation sensor. The method may include displaying at least one ultrasound image obtained from the handheld ultrasound probe. The method may include displaying the current contact force. The method may include stopping the linear drive system in response to detecting an end of travel of the linear drive system along the actuation axis. The method may include receiving an input from a user through a user input during a scan. The user input may include at least one of a button, a switch, and a dial, and wherein the input activates a function including at least one of initiation of a scan, termination of a scan, selection of the current contact force as the desired contact force, storage of the current contact force in a memory for subsequent recall, and recall of the desired contact force from the memory.

The method may include providing at least three modes of operation for the linear drive system including an initiation mode, a controlled-force mode, and a scan termination mode. The initiation mode may include: placing the linear drive system in a neutral position; monitoring the current contact force; and transitioning to a controlled-force mode of operation when the current contact force meets a predetermined threshold. The predetermined threshold may be predictively determined. The scan termination mode may be initiated upon detection of a rapid decrease in the current contact force. The scan termination mode may include moving the linear drive system to a neutral position at a controlled velocity.

A device disclosed herein includes a substantially rigid frame adapted to receive a handheld ultrasound probe; a force sensor mechanically coupled to the frame and configured to sense a force applied to the frame by the handheld ultrasound probe; a linear drive system substantially rigidly coupled to the frame and including a control input, the linear drive system responsive to a control signal received at the control input to translate the frame along an actuation axis; and a controller electronically coupled to the force sensor and the control input of the linear drive system, the controller including processing circuitry configured to generate the control signal to the control input in a manner that maintains a predetermined force between the frame and the handheld ultrasound probe.

The linear drive system and the controller may be configured to compensate for an oscillating hand movement of a user at a frequency between four Hertz and thirty Hertz. The force sensor may have a resolution of at least 0.05 Newtons. The linear drive system may provide an actuation range for the ultrasound transducer of at least six centimeters. The device may include a torque sensor mechanically coupled to the ultrasound probe and electronically coupled to the controller, the torque sensor detecting a torque between the ultrasound probe and the linear drive system. The substantially rigid frame may include a trunk shaped and sized for gripping by a user. The trunk may be oriented parallel to the linear drive system. The device may include a proximity sensor operable to detect a proximity of the handheld ultrasound probe to the subject. The device may include an orientation sensor operable to independently detect at least one of a position and an orientation of the device. The controller may be programmed to vary the predetermined force according to a generalized tent map function.

The device may include a memory to store data from the handheld ultrasound probe and the sensor. The memory may be a remote memory storage device. The device may include a wireless interface for communication with a remote storage device. The controller may be configured to identifying a difference between the predetermined force and the force applied to the frame, and to actuate the linear drive system to reduce the difference. The controller may be operable to achieve predetermined force with a steady state error less than 3% for applied forces ranging from one to seven Newtons. The predetermined force may be constant for a duration of an ultrasound scan. The predetermined force may be less than or equal to twenty Newtons. The predetermined force may vary with time. The linear drive system may include a ballscrew-driven linear actuator and a motor. The device may include two plates positioned to surround and securely affix the handheld ultrasound probe to the substantially rigid frame.

BRIEF DESCRIPTION OF THE FIGURES

The invention and the following detailed description of certain embodiments thereof may be understood by reference to the following figures.

DETAILED DESCRIPTION

The techniques described below allow real-time control of the contact force between an ultrasound probe and a target, such as a patient's body. This allows ultrasound technicians to take fixed- or variably-controlled-contact-force ultrasound measurements of the target, as desired.

Figure 1:
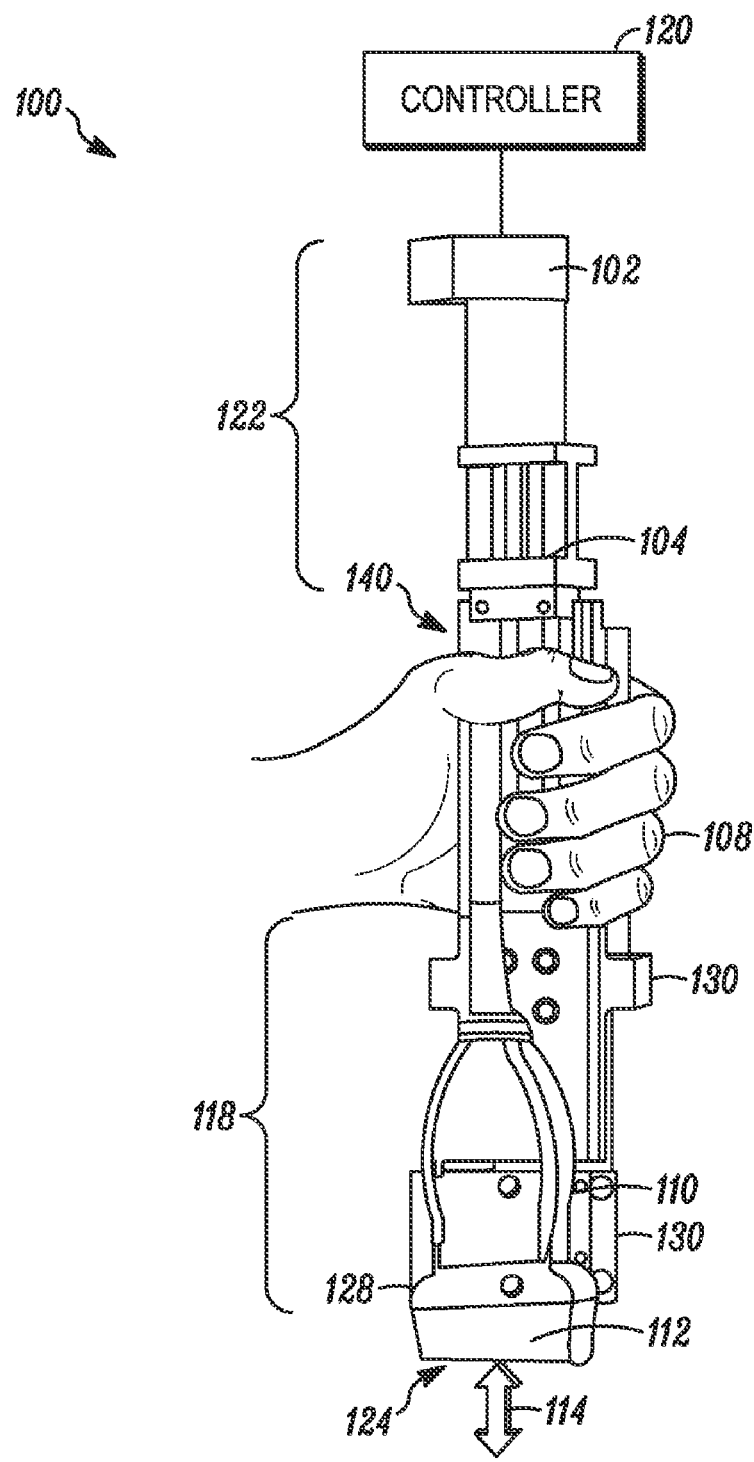
FIG. 1 is a perspective view of a handheld ultrasound probe control device.

FIG. 1 is a perspective view of a handheld ultrasound probe control device. The device 100 may include a frame 118 adapted to receive a probe 112, a linear drive system 122 that translates the frame 118 along an actuation axis 114, a sensor 110 such as a force sensor, a torque sensor, or some combination of these, and a controller 120.

The probe 112 can be of any known type or construction. The probe 112 may, for example include a handheld ultrasound probe used for medical imaging or the like. More generally, the probe 112 may include any contact scanner or other device that can be employed in a manner that benefits from the systems and methods described herein. Thus, one advantage of the device 100 is that a standard off-the-shelf ultrasound medical probe can be retrofitted for use as a force-controlled ultrasound in a relatively inexpensive way; i.e., by mounting the probe 112 in the frame 118. Medical ultrasound devices come in a variety of shapes and sizes, and the frame 118 and other components may be adapted for a particular size/shape of probe 112, or may be adapted to accommodate a varying sizes and/or shapes. In another aspect, the probe 112 may be integrated into the frame 118 or otherwise permanently affixed to or in the frame 118.

In general, a probe 112 such as an ultrasound probe includes an ultrasound transducer 124. The construction of suitable ultrasound transducers is generally well known, and a detailed description is not required here. In one aspect, an ultrasound transducer includes piezoelectric crystals or similar means to generate ultrasound waves and/or detect incident ultrasound. More generally, any suitable arrangement for transmitting and/or receiving ultrasound may be used as the ultrasound transducer 124. Still more generally, other transceiving mechanisms or transducers may also or instead be used to support imaging modalities other than ultrasound.

The frame 118 may include any substantially rigid structure that receives and holds the probe 112 in a fixed position and orientation relative to the frame 118. The frame 118 may include an opening that allows an ultrasound transducer 124 of the probe 112 to contact a patient's skin or other surface through which ultrasound images are to be obtained. Although FIG. 1 shows the probe 112 held within the frame 118 between two plates (a front plate 128 bolted to a larger plate 130 on the frame 118) arranged to surround a handheld ultrasound probe and securely affix the probe to the frame 118, any suitable technique may also or instead be employed to secure the probe 112 in a fixed relationship to the frame 118. For example, the probe 112 may be secured with a press fit, hooks, screws, anchors, adhesives, magnets, or any combination of these and other fasteners. More generally, the frame 118 may include any structure or combination of structure suitable for securely retaining the probe 112 in a fixed positional relationship relative to the probe 112.

In one aspect, the frame 118 may be adapted for handheld use, and more particularly adapted for gripping by a technician in the same orientation as a conventional ultrasound probe. Without limitation, this may include a trunk 140 or the like for gripping by a user that extends axially away from the ultrasound transducer 124 and generally normal to the contact surface of the transducer 124. Stated alternatively, the trunk 140 may extend substantially parallel to the actuation axis 114 and be shaped and sized for gripping by a human hand. In this manner, the trunk 140 may be gripped by a user in the same manner and orientation as a typical handheld ultrasound probe. The linear drive system 122 may advantageously be axially aligned with the trunk 140 to permit a more compact design consistent with handheld use. That is, a ballscrew or similar linear actuator may be aligned to pass through the trunk 140 without diminishing or otherwise adversely affecting the range of linear actuation.

The linear drive system 122 may be mounted on the device 100 and may include a control input electronically coupled to the controller 120. The linear drive system 122 may be configured to translate the probe 112 along an actuation axis 114 in response to a control signal from the controller 120 to the control input of the linear drive system 122. Although the linear drive system 122 is depicted by way of example as a motor 102 and a linear actuator 104, any system capable of linearly moving the probe 112 can be employed. For example, the linear drive system 122 can include a mechanical actuator, hydraulic actuator, pneumatic actuator, piezoelectric actuator, electro-mechanical actuator, linear motor, telescoping linear actuator, ballscrew-driven linear actuator, and so on. More generally, any actuator or combination of actuators suitable for use within a grippable, handheld form factor such as the trunk 140 may be suitably employed as the linear drive system 122. In some implementations, the linear drive system 122 is configured to have a low backlash (e.g., less than 3 µm) or no backlash in order to improve positional accuracy and repeatability.

The ability of the probe 112 to travel along the actuation axis 114 permits the technician flexibility in hand placement while using the device 100. In some implementations, the probe 112 can travel up to six centimeters along the actuation axis 114, although greater or lesser ranges of travel may be readily accommodated with suitable modifications to the linear actuator 104 and other components of the device 100.

The motor 102 may be electrically coupled to the controller 120 and mechanically coupled in a fixed positional relationship to the linear actuator 104. The motor 102 may be configured to drive the linear actuator 104 in response to control signals from the controller 120, as described more fully below. The motor 102 can include a servo motor, a DC stepper motor, a hydraulic pump, a pneumatic pump, and so on.

The sensor 110, which may include a force sensor and/or a torque sensor, may be mechanically coupled the frame 118, such as in a fixed positional relationship to sense forces/torques applied to the frame 118. The sensor 110 may also be electronically coupled to the controller 120, and configured to sense a contact force between the probe 112 and a target surface (also referred to herein simply as a "target") such as a body from which ultrasound images are to be captured. As depicted, the sensor 110 may be positioned between the probe 112 and the back plate of the frame 118. Other deployments of the sensor 110 are possible, so long as the sensor 110 is capable of detecting the contact force (for a force sensor) between the probe 112 and the target surface. Embodiments of the sensor 110 may also or instead include a multi-axis force/torque sensor, a plurality of separate force and/or torque sensors, or the like.

The sensor 110 can provide output in any known form, and generally provides a signal indicative of forces and/or torques applied to the sensor 110. For example, the sensor 110 can produce analog output such as a voltage or current proportional to the force or torque detected. Alternatively, the sensor 110 may produce digital output indicative of the force or torque detected. Moreover, digital-to-analog or analog-to-digital converters (not shown) can be deployed at any point between the sensors and other components to convert between these modes. Similarly, the sensor 110 may provide radio signals (e.g., for wireless configurations), optical signals, or any other suitable output that can characterize forces and/or torques for use in the device 100 described herein.

The controller 120 generally includes processing circuitry to control operation of the device 100 as described herein. The controller 120 may receive signals from the sensor 110 indicative of force/torque, and may generate a control signal to a control input of the linear drive system 122 (or directly to the linear actuator 104) for maintaining a given contact force between the ultrasound probe 112 and the target, as described more fully below. The controller 120 may include analog or digital circuitry, computer program code stored in a non-transitory computer-readable storage medium, and so on. Embodiments of the controller 120 may employ pure force control, impedance control, contact force-determined position control, and so on.

The controller 120 may be configured with preset limits relating to operational parameters such as force, torque, velocity, acceleration, position, current, etc. so as to immediately cut power from the linear drive system 122 when any of these operational parameters exceed the preset limits. In some implementations, these preset limits are determined based on the fragility of the target. For example, one set of preset limits may be selected where the target is a healthy human abdomen, another set of preset limits may be selected where the target is a human abdomen of an appendicitis patient, etc. In addition, preset limits for operational parameters may be adjusted to accommodate discontinuities such as initial surface contact or termination of an ultrasound scan (by breaking contact with a target surface).

In some implementations, the device 100 includes a servo-motor-driven ballscrew linear actuator comprising a MAXON servo motor (EC-Max #272768) (motor 102) driving an NSK MONOCARRIER compact ballscrew actuator (linear actuator 104); a MINI40 six-axis force/torque sensor (sensor 110) from ATI INDUSTRIAL AUTOMATION, which simultaneously monitors all three force and all three torque axes, is mounted to the carriage of the actuator, and a TERASON 5 MHz ultrasound transducer (ultrasound transducer 124) is mounted to the force/torque sensor.

The vector from a geometric origin of the sensor 110 to an endpoint at the probe 124 that contacts a patient can be used to map the forces and torques at the sensor 110 into the contact forces and torques seen at the probe/patient interface. In some implementations, it is possible to maintain a set contact force with a mean error of less than 0.2% and, in a closed-loop system, maintain a desired contact force with a mean steady state error of about 2.1%, and attain at least 20 Newtons of contact force. More generally, in one embodiment a steady state error of less than 3% was achieved for applied forces ranging from one to seven Newtons.

Other sensors (indicated generically as a second sensor 130) may be included without departing from the scope of this invention. For example, a second sensor 130 such as an orientation sensor or the like may be included, which may be operable to independently detect at least one of a position and an orientation of the device 100, such as to track location and/or orientation of the device 100 before, during, and after use. This data may help to further characterize operation of the device 100. A second sensor 130 such as a range or proximity detector may be employed to anticipate an approaching contact surface and place the device 100 in a state to begin an ultrasound scan. For example, a proximity sensor may be operable to detect a proximity of the ultrasound transducer 124 to a subject (e.g., the target surface). More generally, any of a variety of sensors known in the art may be used to augment or supplement operation of the device 100 as contemplated herein.

Figure 2:
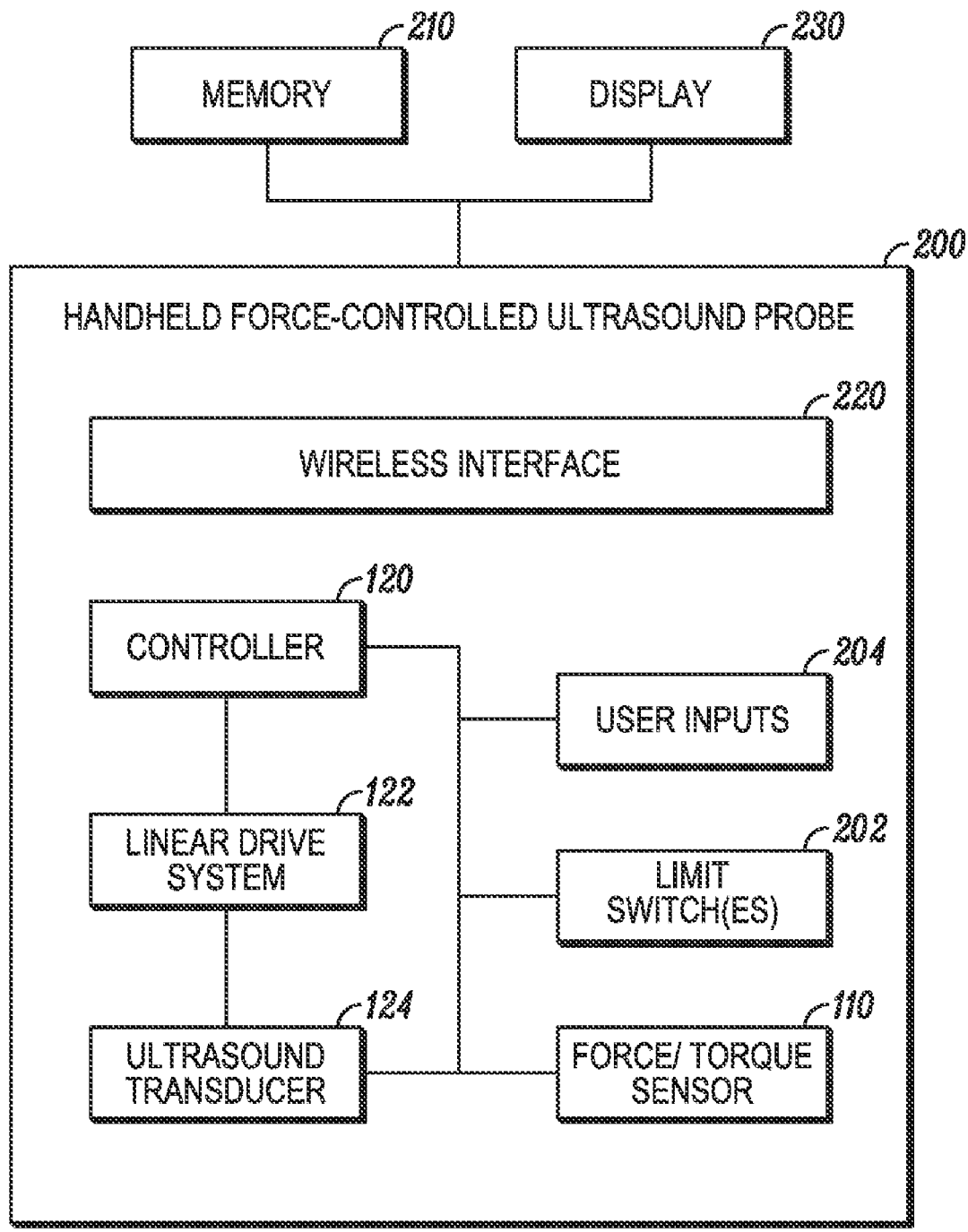
FIG. 2 is a schematic view of a handheld ultrasound probe.

FIG. 2 is a schematic depiction of a handheld force-controlled ultrasound probe. The probe 200, which may be a force-controlled ultrasound probe as generally described herein, generally includes a sensor 110, a controller 120, a linear drive system 122, and an ultrasound transducer 124 as described above.

In contrast to the probe 112 mounted in the device 100 as described in FIG. 1, the probe 200 of FIG. 2 has the sensor 110, controller 120, and linear drive system 122 integrally mounted (as opposed to mounted in a separate device 100) in a single device to provide a probe 200 with an integral structure. In FIG. 2, the components are all operable to gather ultrasound images at measured and/or controlled forces and torques, as described above with reference to FIG. 1. More generally, the various functions of the above-described components may be distributed across several independent devices in various ways (e.g., an ultrasound probe with integrated force/torque sensors but external drive system, an ultrasound probe with an internal drive system but external control system, etc.). In one aspect, a wireless handheld probe 200 may be provided that transmits sensor data and/or ultrasound data wirelessly to a remote computer that captures data for subsequent analysis and display. All such permutations should be considered to be within the scope of this disclosure.

The ultrasound transducer 124 can include a medical ultrasonic transducer, an industrial ultrasonic transducer, or the like. Like the ultrasound probe 112 described above with reference to FIG. 1, it will be appreciated that a variety of embodiments of the ultrasound transducer 124 are possible, including embodiments directed to non-medical applications such as nondestructive ultrasonic testing of materials and objects and the like, or more generally, transducers or other transceivers or sensors for capturing data instead of or in addition to ultrasound data. Thus, although reference is made to an "ultrasound probe" in this document, the techniques described herein are more generally applicable to any context in which the transmission of energy (e.g., sonic energy, electromagnetic energy, thermal energy, etc.) from or through a target varies as a function of the contact force between the energy transmitter and the target.

Other inputs/sensors may be usefully included in the probe 200. For example, the probe 200 may include a limit switch 202 or multiple limit switches 202. These may be positioned at any suitable location to detect limits of travel of the linear drive system 122, and used to prevent damage or other malfunction of the linear drive system 122 or other system components. The limit switch(es) may be electronically coupled to the controller 120 and provide a signal to the controller 120 to indicate when the limit switch 122 detects an end of travel of the linear drive system along the actuation axis. The limit switch 122 may include any suitable electro-mechanical sensor or combination of sensors such as a contact switch, proximity sensor, range sensor, magnetic coupling, and so forth.

The probe 200 may also or instead include one or more user inputs 204. These may be physically realized by buttons, switches, dials, or the like on the probe 200. The user inputs 204 may be usefully positioned in various locations on an exterior of the probe 200. For example, the user inputs 204 may be positioned where they are readily finger-accessible while gripping the probe 200 for a scan. In another aspect, the user inputs 204 may be positioned away from usual finger locations so that they are not accidentally activated while manipulating the probe 200 during a scan. The user inputs 204 may generally be electronically coupled to the controller 120, and may support or activate functions such as user identification of initiation of a scan, termination of a scan, selection of a current contact force as the target contact force, storage of a current contact force in memory for subsequent recall, or recall of a predetermined contact force from memory. Thus, a variety of functions may be usefully controlled by a user with the user inputs 204.

A memory 210 may be provided to store ultrasound data from the ultrasound transducer and/or sensor data acquired from any of the sensors during an ultrasound scan. The memory 210 may be integrally built into the probe 200 to operate as a standalone device, or the memory 210 may include remote storage, such as in a desktop computer or other device with suitable storage capacity. In one aspect, data may be wirelessly transmitted from the probe 200 to the memory 210 to permit wireless operation of the probe 200. The probe 200 may include any suitable wireless interface 220 to accommodate such wireless operation, such as for wireless communications with a remote storage device (which may include the memory 210).

A display 230 may be provided, which may receive wired or wireless data from the probe 200. The display 230 and memory 210 may be a display and memory of a desktop computer or the like, or may be standalone accessories to the probe 200, or may be integrated into a medical imaging device that includes the probe 200, memory 210, display 230 and any other suitable hardware, processor(s), and the like. The display 230 may display ultrasound images obtained from the probe 200 using known techniques. The display 230 may also or instead display a current contact force or instantaneous contact force measured by the sensor 110, which may be displayed superimposed on a corresponding ultrasound image or in another display region of the display 230. Other useful information, such as a target contact force, an actuator displacement, or an operating mode, may also or instead be usefully rendered on the display 230 to assist a user in obtaining ultrasound images.

Figure 3:
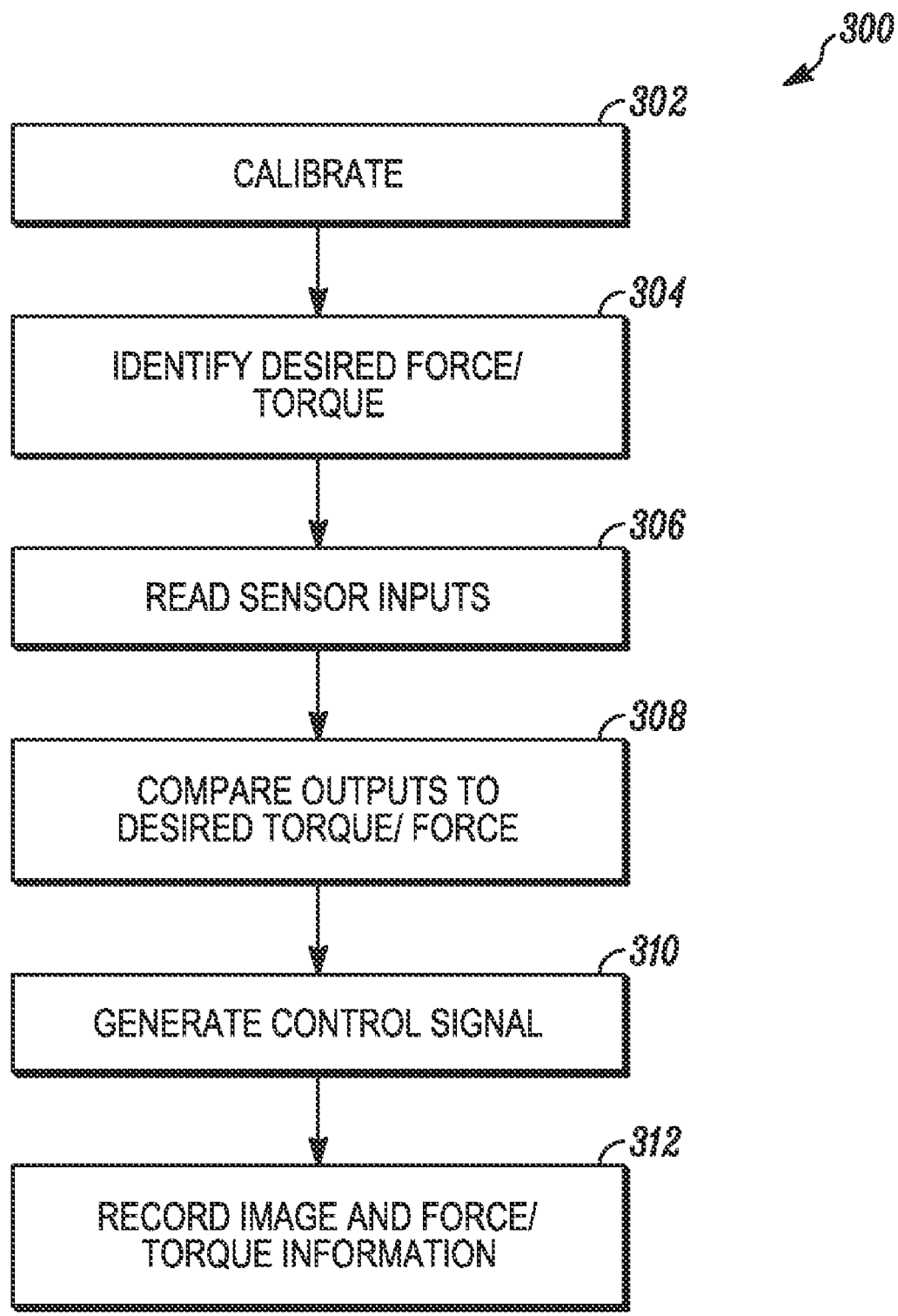
FIG. 3 is a flowchart for a process for force-controlled acquisition of ultrasound images.

FIG. 3 is a flowchart for a process for force-controlled acquisition of ultrasound images. In some implementations, the process 300 can be performed using a handheld ultrasound probe 112 mounted in a device 100, or a handheld ultrasound probe 200 with integrated force control hardware.

The process 300 begins by calibrating the force and/or torque sensors (step 302). The calibration step is for minimizing (or ideally, eliminating) errors associated with the weight of the ultrasound probe or the angle at which the sensors are mounted with respect to the ultrasound transducer.

To compensate for the mounting angle, the angle between the sensor axis and the actuation axis may be independently measured (e.g., when the sensor is installed). This angle may be subsequently stored for use by the controller to combine the measured forces and/or torques along each axis into a single vector, using standard coordinate geometry. (E.g., for a mounting angle $\theta$, scaling the appropriate measured forces by $\sin(\theta)$ and $\cos(\theta)$ prior to combining them.)

To compensate for the weight of the ultrasound probe, a baseline measurement may be taken, during a time at which the ultrasound probe is not in contact with the target. Any measured force may be modeled as due either to the weight of the ultrasound probe, or bias inherent in the sensors. In either case, the baseline measured force may be recorded, and may be subtracted from any subsequent force measurements.

In step 304, a predetermined desired force may be identified. In some implementations, the desired force is simply a constant force. For example, in imaging a human patient, a constant force of less than or equal 20 Newtons is often desirable for the comfort and safety of the patient.

In some implementations, the desired force may vary as a function of time. For example, it is often useful to "poke" a target in a controlled manner, and acquire images of the target as it deforms during or after the poke. In some implementations, the desired force may involve a gradual increase of force given by a function $F(t)$ to a force $F_{max}$ at a time $t_{max}$, and then a symmetric reduction of force until the force reaches zero. Such a function is often referred to as a "generalized tent map," and may be given by the function $G(t)=F(t)$ if $t<t_{max}$, and $G(t)=F_{max}-F(t-t_{max})$ for $t \geq t_{max}$. When F is a linear function, the graph of G(t) resembles a tent, hence the name. In another aspect, a desired force function may involve increasing the applied force by some function $F(t)$ for a specified time period until satisfactory imaging (or patient comfort) is achieved, and maintaining that force thereafter until completion of a scan. The above functions are given by way of example. In general, any predetermined force function can be used.

The output of the force and/or torque sensors are read (step 306) and compared to the desired force function (step 308) to determine a force differential. In some implementations, the comparison can be accomplished by computing the difference of the sensor output with the corresponding desired sensor output. Similarly, the ratio of output to the desired output can be computed. Many other functions can be used.

In step 310, a control signal may be generated based on the comparison of step 308. The control signal may be such that the linear drive system is activated in such a way as to cause the measured force and/or torque to be brought closer to the desired force and/or torque at a given time. For example, if the difference of the measured force and the desired force were computed in step 308, then the drive system can translate the probe with a force whose magnitude is proportional to the difference, in the direction of minimizing the difference. Similarly, if the ratio of the desired force and measured force were computed in step 308, then the drive system can translate the probe with a force whose magnitude is proportional to one minus this ratio.

More generally, any known techniques from control theory can be used to drive the measured force towards the desired force. These techniques include linear control algorithms, proportional-integral-derivative ("PID") control algorithms, fuzzy logic control algorithms, etc. By way of example, the control signal may be damped in a manner that avoids sharp movements of the probe against a patient's body. In another aspect, the closed-loop control system may be adapted to accommodate ordinary variations in a user's hand position. For example, a human hand may typically have small positional variations with an oscillating frequency of about four Hertz to about twenty Hertz. As such, the controller may be configured to compensate for an oscillating hand movement of a user at a frequency between four Hertz and thirty Hertz or any other suitable range. Thus, the system may usefully provide a time resolution finer than twenty Hertz or thirty Hertz, accompanied by an actuation range within the time resolution larger than typical positional variations associated with jitter or tremors in an operator's hand.

In parallel with steps 302-310, as shown in step 312, the ultrasound probe can acquire an image, a fraction of an image, or more than one image. The image(s) (or fractions thereof) may be stored together with contact force and/or torque information applicable during the image acquisition. In some implementations, the contact force and/or torque information includes all the information produced by the force and/or torque sensors; i.e., the moment-by-moment output of the sensors over the time period during which the image was acquired. In some implementations, other derived quantities can be computed and stored, such as the average or mean contact force and/or torque, the maximum or minimum contact force and/or torque, etc.

It will be understood that the steps of the above methods may be varied in sequence, repeated, modified, or deleted, or additional steps may be added, all without departing from the scope of this disclosure. By way of example, the step of identifying a desired force may be performed a single time where a constant force is required, or continuously where a time-varying applied force is desired. In addition, operation of the probe in clinical settings may include various modes of operation each having different control constraints. Some of these modes are described below with reference to FIG. 5. Thus, the details of the foregoing will be understood as non-limiting examples of the systems and methods of this disclosure.

Figure 4:
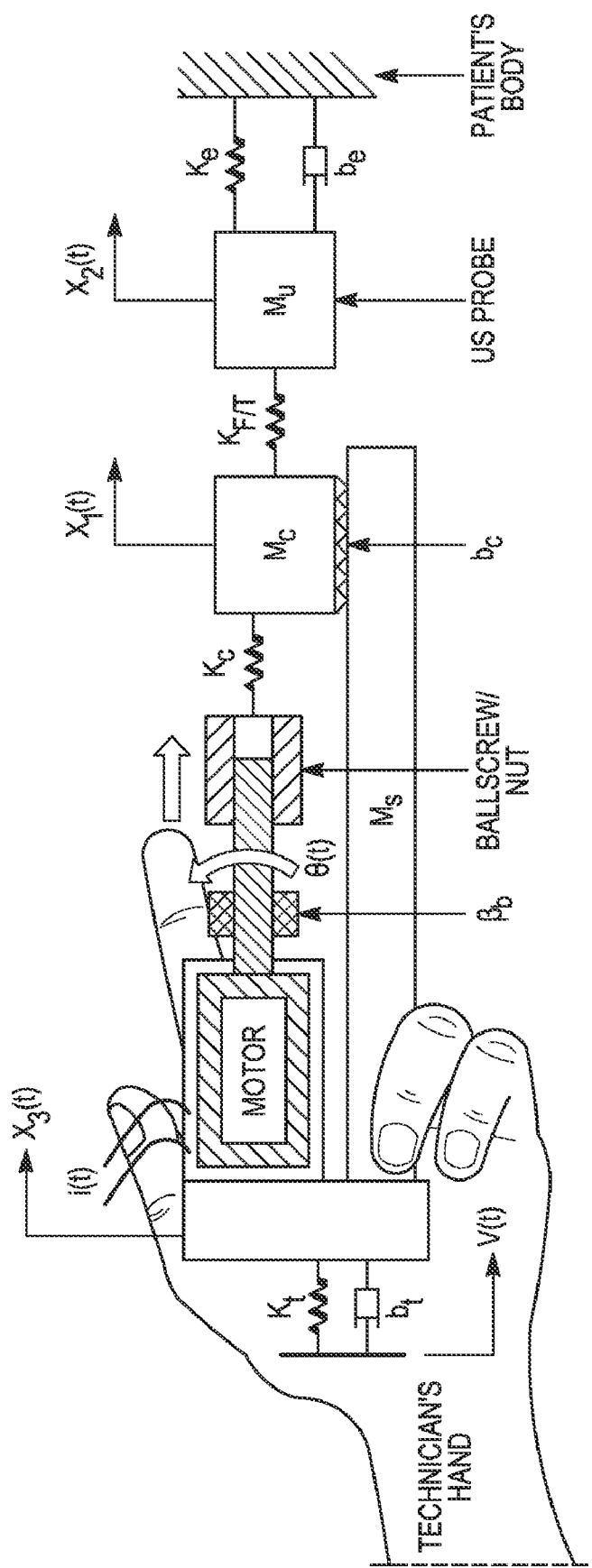
FIG. 4 depicts a lumped parameter model of the mechanical system of a probe as described herein.

FIG. 4 depicts a lumped parameter model of the mechanical system of a probe as described herein. While a detailed mathematical derivation is not provided herein, and the lumped model necessarily abstracts away some characteristics of an ultrasound probe, the model of FIG. 4 provides a useful analytical framework for creating a control system that can be realized using the controller and other components described above to achieve force-controlled acquisition of ultrasound images.

In general, the model 400 characterizes a number of lumped parameters of a controlled-force probe. The physical parameters for an exemplary embodiment are as follows. $M_u$ is the mass of ultrasound probe and mounting hardware, which may be 147 grams. $M_c$ is the mass of a frame that secures the probe, which may be 150 grams. $M_s$, is the mass of the linear drive system, which may be 335 grams. $k_{F/T}$ is the linear stiffness of a force sensor, which may be $1.1*10^5$ N/m. $k_e$ is the target skin stiffness, which may be 845N/m. $b_e$ is the viscous damping coefficient of the target, which may be 1500 Ns/m. $k_t$ is the user's total limb stiffness, which may be 1000 N/m. $b_t$ is the user's total limb viscous damping coefficient, which may be 5000 Ns/m. $b_c$ is the frame viscous damping coefficient, which may be 0 Ns/m. $k_C$ is the stiffness of the linear drive system, which may be $3*10^7$ for an exemplary ballscrew and nut drive. $K_T$ is the motor torque constant, which may be 0.0243 Nm/A. $\beta_b$ is be the linear drive system viscous damping, which may be $2*10^{-4}$ for an exemplary ball screw and motor rotor. L is the linear drive system lead, which may be $3*10^{-4}$ for an exemplary ballscrew. $J_{tot}$ is the moment of inertia, which may be $1.24*10^{-6}$ kgm$^2$ for an exemplary ballscrew and motor rotor.

Using these values, the mechanical system can be mathematically modeled, and a suitable control relationship for implementation on the controller can be determined that permits application of a controlled force to the target surface by the probe. Stated differently, the model may be employed to relate displacement of the linear drive system to applied force in a manner that permits control of the linear drive system to achieve an application of a controlled force to the target surface. It will be readily appreciated that the lumped model described above is provided by way of illustration and not limitation. Variations may be made to the lumped model and the individual parameters of the model, either for the probe described above or for probes having different configurations and characteristics, and any such model may be usefully employed provided it yields a control model suitable for implementation on a controller as described above.

Figure 5:
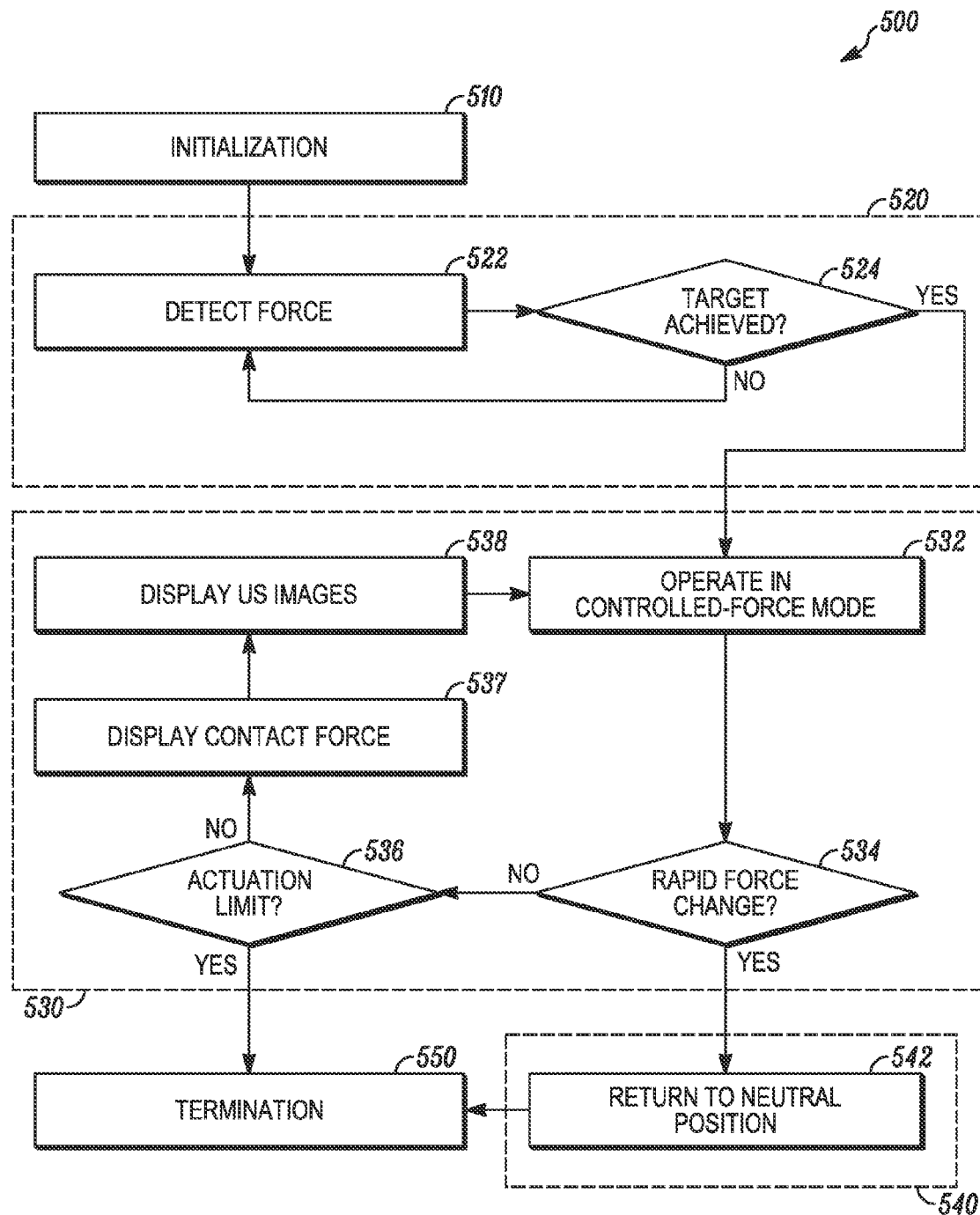
FIG. 5 is a flowchart depicting operating modes of a force-controlled ultrasound probe.

FIG. 5 is a flowchart depicting operating modes of a force-controlled ultrasound probe. While the probe described above may be usefully operated in a controlled-force mode as discussed above, use of the handheld probe in clinical settings may benefit from a variety of additional operating modes for varying circumstances such as initial contact with a target surface or termination of a scan. Several useful modes are now described in greater detail.

In general, the process 500 includes an initialization mode 510, a scan initiation mode 520, a controlled-force mode 530, and a scan termination mode 540, ending in termination 550 of the process 500.

As shown in step 510, an initialization may be performed on a probe. This may include, for example, powering on various components of the probe, establishing a connection with remote components such as a display, a memory, and the like, performing any suitable diagnostic checks on components of the probe, and moving a linear drive system to a neutral or ready position, which may for example be at a mid-point of a range of movement along an actuation axis.

As shown in step 522, the initiation mode 520 may begin by detecting a force against the probe using a sensor, such as any of the sensors described above. In general, prior to contact with a target surface such as a patient, the sensed force may be at or near zero. In this state, it would be undesirable for the linear drive system to move to a limit of actuation in an effort to achieve a target controlled force. As such, the linear drive system may remain inactive and in a neutral or ready position during this step.

As shown in step 524, the controller may check to determine whether the force detected in step 522 is at or near a predetermined contact force such as the target contact force for a scan. If the detected force is not yet at (or sufficiently close to) the target contact force, then the initiation mode 520 may return to step 522 where an additional force measurement is acquired. If the force detected in step 522 is at or near the predetermined contact force, the process 500 may proceed to the controlled-force mode 530. Thus, a controller disclosed herein may provide an initiation mode in which a linear drive system is placed in a neutral position and a force sensor is measured to monitor an instantaneous contact force, the controller transitioning to controlled-force operation when the instantaneous contact force meets a predetermined threshold. The predetermined threshold may be the predetermined contact force that serves as the target contact force for controlled-force operation, or the predetermined threshold may be some other limit such as a value sufficiently close to the target contact force so that the target contact force can likely be readily achieved through actuation of the linear drive system. The predetermined threshold may also or instead be predictively determined, such as by measuring a change in the measured contact force and extrapolating (linearly or otherwise) to estimate when the instantaneous contact force will equal the target contact force.

As shown in step 532, the controlled-force mode 530 may begin by initiating controlled-force operation, during which a control system may be executed in the controller to maintain a desired contact force between the probe and a target, all as generally discussed above.

While in the controlled-force mode 530, periodic functions may be performed. For example, as shown in step 534, the current contact force may be monitored for rapid changes. In general, a rapid decrease in contact force may be used to infer that a probe operator has terminated a scan by withdrawing the probe from contact with a target surface. This may be for example, a step decrease in measured force to zero, or any other pattern of measured force that deviates significantly from expected values during an ongoing ultrasound scan. If there is a rapid change in force, then the process 500 may proceed to the termination mode 540. It will be appreciated that this transition may be terminated where the force quickly returns to expected values, and the process may continue in the controlled-force mode 530 even where there are substantial momentary variations in measure force. As s shown in step 536, limit detectors for a linear drive system may be periodically (or continuously) monitored to determine whether an actuation limit of the linear drive system has been reached. If no such limit has been reached, the process 500 may continue in the controlled-force mode 530 by proceeding for example to step 537. If an actuation limit has been reached, then the process may proceed to termination 550 where the linear drive system is disabled. It will be appreciated that the process 500 may instead proceed to the termination mode 540 to return the linear drive system to a neutral position for future scanning.

As shown in step 537, a contact force, such as measured with any of the force sensors described above, may be displayed in a monitor or the like. The contact force may, for example, be displayed alongside a target contact force or other data. As shown in step 538, ultrasound images may be displayed using any known technique, which display may be alongside or superimposed with the force data and other data described above.

As shown in step 542, when a rapid force change or other implicit or explicit scan termination signal is received, the process 500 may enter a scan termination mode 540 in which the linear drive system returns to a neutral or ready position using any suitable control algorithm, such as a controlled-velocity algorithm that returns to a neutral position (such as a mid-point of an actuation range) at a constant, predetermined velocity. When the linear drive system has returned to the ready position, the process 500 may proceed to termination as shown in step 550, where operation of the linear drive system is disabled or otherwise terminated.

Thus, it will be appreciated that a method or system disclosed herein may include operation in at least three distinct modes to accommodate intuitive user operation during initiation of a scan, controlled-force scanning, and controlled-velocity exit from a scanning mode. Variations to each mode will be readily envisioned by one of ordinary skill in the art and are intended to fall within the scope of this disclosure. Thus, for example any one of the modes may be entered or exited by explicit user input. In addition, the method may accommodate various modes of operation using the sensors and other hardware described above. For example the controlled-force mode 530 may provide for user selection or input of a target force for controlled operation using, e.g., any of the user inputs described above.

More generally, the steps described above may be modified, reordered, or supplemented in a variety of ways. By way of example, the controlled-force mode of operation may include a controlled-velocity component that limits a rate of change in position of the linear drive system. Similarly, the controlled-velocity mode for scan termination may include a controlled-force component that checks for possible recovery of controlled-force operation while returning the linear drive system to a neutral position. All such variations, and any other variations that would be apparent to one of ordinary skill in the art, are intended to fall within the scope of this disclosure.

It will be appreciated that many of the above systems, devices, methods, processes, and the like may be realized in hardware, software, or any combination of these suitable for the data processing, data communications, and other functions described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as the handheld probe and a remote desktop computer or storage device, or all of the functionality may be integrated into a dedicated, standalone device including without limitation a wireless, handheld ultrasound probe. All such permutations and combinations are intended to fall within the scope of the present disclosure.

In other embodiments, disclosed herein are computer program products comprising computer-executable code or computer-usable code that, when executing on one or more computing devices (such as the controller described above), performs any and/or all of the steps described above. The code may be stored in a computer memory or other non-transitory computer readable medium, which may be a memory from which the program executes (such as internal or external random access memory associated with a processor), a storage device such as a disk drive, flash memory or any other optical, electromagnetic, magnetic, infrared or other device or combination of devices. In another aspect, any of the processes described above may be embodied in any suitable transmission or propagation medium carrying the computer-executable code described above and/or any inputs or outputs from same.

While particular embodiments of the present invention have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method of acquiring ultrasound images of a target using a handheld ultrasound probe comprising:
    identifying a predetermined, desired contact force between the handheld ultrasound probe and a target;
    measuring a current contact force between the handheld ultrasound probe and the target;
    comparing the current contact force to the desired contact force, thereby identifying a force differential;
    actuating a linear drive system to move the handheld ultrasound probe along an actuation axis so as to reduce the force differential and
    providing at least three modes of operation for the linear drive system including an initiation mode, a controlled-force mode, and a scan termination mode, wherein the scan termination mode is initiated upon detection of a rapid decrease in the current contact force.

2. The method of claim 1, further comprising calibrating at least one of a force sensor and a torque sensor mechanically coupled to the handheld ultrasound probe to account for a weight of the handheld ultrasound probe.

3. The method of claim 1, further comprising calibrating at least one of a force sensor and a torque sensor mechanically coupled to the handheld ultrasound probe to account for a mounting angle of the ultrasound probe.

4. The method of claim 1, wherein the predetermined desired contact force is constant.

5. The method of claim 4, wherein the predetermined desired contact force is less than or equal to twenty Newtons.

6. The method of claim 1, wherein the predetermined desired contact force varies with time.

7. The method of claim 6, wherein the predetermined desired contact force varies according to a generalized tent map function.

8. The method of claim 1 further comprising wirelessly transmitting ultrasound data to a remote storage facility.

9. The method of claim 1 further comprising detecting a proximity of the handheld ultrasound probe to the target.

10. The method of claim 1 further comprising detecting at least one of a position and an orientation of the handheld ultrasound probe using an orientation sensor.

11. The method of claim 1 further comprising displaying at least one ultrasound image obtained from the handheld ultrasound probe.

12. The method of claim 11 further comprising displaying the current contact force.

13. The method of claim 1 further comprising stopping the linear drive system in response to detecting an end of travel of the linear drive system along the actuation axis.

14. The method of claim 1 further comprising receiving an input from a user through a user input during a scan.

15. The method of claim 14 wherein the user input includes at least one of a button, a switch, and a dial, and wherein the input activates a function including at least one of initiation of a scan, termination of a scan, selection of the current contact force as the desired contact force, storage of the current contact force in a memory for subsequent recall, and recall of the desired contact force from the memory.

16. The method of claim 1 wherein the initiation mode includes:

placing the linear drive system in a neutral position;

monitoring the current contact force; and transitioning to a controlled-force mode of operation when the current contact force meets a predetermined threshold.

17. The method of claim 16 wherein the predetermined threshold is predictively determined.

18. The method of claim 1 wherein the scan termination mode includes moving the linear drive system to a neutral position at a controlled velocity.

* * * * *